United States Patent
Li et al.

(10) Patent No.: US 11,885,186 B2
(45) Date of Patent: Jan. 30, 2024

(54) HIGH-TEMPERATURE AND HIGH-PRESSURE DRILLING FLUID INHIBITION EVALUATION DEVICE AND USAGE METHOD THEREOF

(71) Applicants: Southwest Petroleum University, Chengdu (CN); CHENGDU KANGPUSHEN PETROLEUM TECHNOLOGY DEVELOPMENT CO., LTD, Sichuan (CN)

(72) Inventors: Xiangchen Li, Chengdu (CN); Yousheng Chen, Chengdu (CN); Fan Zhang, Chengdu (CN)

(73) Assignees: Southwest Petroleum University, Chengdu (CN); CHENGDU KANGPUSHEN PETROLEUM TECHNOLOGY DEVELOPMENT CO., LTD, Sichuan (CN)

( * ) Notice: Subject to any disclaimer, the term of this patent is extended or adjusted under 35 U.S.C. 154(b) by 0 days.

(21) Appl. No.: 17/778,431

(22) PCT Filed: Dec. 10, 2021

(86) PCT No.: PCT/CN2021/137098
§ 371 (c)(1),
(2) Date: May 20, 2022

(87) PCT Pub. No.: WO2022/122017
PCT Pub. Date: Jun. 16, 2022

(65) Prior Publication Data
US 2023/0131487 A1   Apr. 27, 2023

(30) Foreign Application Priority Data
Dec. 11, 2020 (CN) .......................... 202011458451.1

(51) Int. Cl.
*E21B 21/08* (2006.01)

(52) U.S. Cl.
CPC .......... *E21B 21/08* (2013.01); *E21B 2200/20* (2020.05)

(58) Field of Classification Search
CPC .......................... E21B 21/08; E21B 2200/20
(Continued)

(56) References Cited

U.S. PATENT DOCUMENTS 3,924,451 A * 12/1975 Drnevich ............... G01N 33/24
                                                          73/594
4,528,842 A *  7/1985 Brown .................. E21B 47/085
                                                          73/152.49
(Continued)

FOREIGN PATENT DOCUMENTS

CN           101482009 A        7/2009
CN           102384966 A        3/2012
(Continued)

*Primary Examiner* — John Fitzgerald
*Assistant Examiner* — Rodney T Frank (57) ABSTRACT

A drilling fluid inhibition evaluation device includes a main test member, a temperature control pressurization system, a gas source, a circulation heating system, a confining pressure pump, a central control system, a computer, an ultrasonic detector and a safety valve electrically connected through pipelines, respectively, the main test member and the temperature control pressurization system sequentially connected with the gas source; the present disclosure can pre-pressurize experimental fluid and then inject the fluid into a dilatometer, so as to prevent the fluid from generating obvious changes of phase states, eliminate pressure setting errors caused by a saturated vapor pressure of the fluid, improve accuracy of evaluation results, inspect a real expansion state of the sample and simultaneously monitor structural change characteristics of a rock sample in real time through reflection conditions of sound waves.

6 Claims, 4 Drawing Sheets

(58) Field of Classification Search
USPC .......................................................... 73/866.4
See application file for complete search history.

(56) References Cited

U.S. PATENT DOCUMENTS

| | | | | |
|---|---|---|---|---|
| 4,734,649 | A * | 3/1988 | Barnaby | G01N 33/241 324/698 |
| 10,900,945 | B2 * | 1/2021 | Hakimuddin | G01N 33/241 |
| 2008/0207970 | A1 * | 8/2008 | Meurer | E21B 41/0064 585/24 |
| 2008/0230219 | A1 * | 9/2008 | Kaminsky | E21B 43/305 166/248 |
| 2010/0095742 | A1 * | 4/2010 | Symington | E21B 41/0064 73/788 |
| 2011/0295509 | A1 * | 12/2011 | Huynh | E21B 21/00 702/12 |
| 2014/0007695 | A1 * | 1/2014 | Darbe | G01N 3/12 73/803 |
| 2019/0383786 | A1 * | 12/2019 | Hugghins | E21B 25/00 |
| 2021/0404993 | A1 * | 12/2021 | Alqam | G01F 13/00 |

FOREIGN PATENT DOCUMENTS

| | | |
|---|---|---|
| CN | 102562040 A | 7/2012 |
| CN | 102590284 A | 7/2012 |
| CN | 102639073 A | 8/2012 |
| CN | 202381087 U | 8/2012 |
| CN | 103161455 A | 6/2013 |
| CN | 103758513 A | 4/2014 |
| CN | 103775070 A | 5/2014 |
| CN | 105136837 A | 12/2015 |
| CN | 106153856 A | 11/2016 |
| CN | 107060737 A | 8/2017 |
| CN | 209430192 U | 9/2019 |
| CN | 110707559 A | 1/2020 |
| CN | 111380779 A | 7/2020 |
| EP | 0822163 A2 | 2/1998 |
| GB | 603009 A | 6/1948 |
| SU | 1055866 A | 11/1983 |
| SU | 1154464 A * | 5/1985 |

* cited by examiner

HIGH-TEMPERATURE AND HIGH-PRESSURE DRILLING FLUID INHIBITION EVALUATION DEVICE AND USAGE METHOD THEREOF

BACKGROUND

1. Technical Field

The present disclosure generally relates to the technical field of petroleum and natural gas exploration simulation experiments, and especially relates to a drilling fluid inhibition evaluation device and a usage method thereof.

2. Description of Related Art

Drilling techniques of deep wells and ultra-deep wells mark the development of drilling technologies, and perfection of the drilling fluid technology is closely related to success or failure of deep well drilling. Because a geothermal gradient and a formation pressure gradient exist, the deeper the well is, the higher the temperature and the pressure are, the drilling fluid is likely to lose its original performances at a high temperature, which puts higher requirements on treating agents of the drilling fluid and also puts a challenge on a research of inhibitors of the drilling fluid under conditions of high temperatures and high pressures.

Instability of wellbores is always a technical problem in the drilling engineering of rock sample gas reservoirs, which is induced by hydration expansion and dispersion of rock samples. Therefore, it is necessary to improve the inhibition of the drilling fluid and minimize an incidence rate of complex conditions under the well to the maximum extent, in this way, an important monitoring instrument, namely an expander, is required to play a role of the oil exploitation.

At present, most drilling fluid inhibitor evaluation devices are contact dilatometers. In order to comprehensively investigate inhibition performances of the drilling fluid under the condition of simulating a complex formation, more and more similar devices are introduced related designs with high-temperature and high-pressure resistances, so that the drilling fluid inhibitor evaluation devices are also applied to evaluate the inhibition performance of the drilling fluid under the conditions of high-temperature and high-pressure. In such designs, most methods for introducing high-temperature and high-pressure conditions into a system is to directly inject high-temperature experimental fluid into the system, when the fluid within a closed container is at a high temperature state, a saturation vapor pressure of the fluid per se influences a pressure of the closed container, and for a limited sealed space of the drilling fluid inhibition performance evaluation device, the saturation vapor pressure generated by the fluid at the high-temperature state causes non-negligible change of an experimental set pressure, so that a target pressure will deviate to influence accuracy of measurement. Meanwhile, different sample expansion results are generated when fluids with different characteristics contact a sample, for example, the sample expansion conditions caused by the fluids with different temperatures and concentrations are different. However, a common expander mostly adopts injected liquid and then heats the injected liquid in a pressure-bearing equipment, so that the problems are occurred that the fluid with a normal temperature contacts with a rock sample in advance, and concentration changes caused by instantaneous evaporation when the normal temperature fluid contacts with a high-temperature container, thereby an error occurs between the expander and the rock sample expansion caused by the high-temperature fluid.

On the other hand, in the expansion process that the rock sample is influenced by the liquid, an internal condition of the rock sample is constantly changed. If a change process of structures of the rock sample during the expansion can be collected and researched, an adaptation condition of the drilling fluid to the rock sample can be further researched and evaluated, so that the inhibitor required by the drilling fluid can be better determined. However, there is no effective use of this function in similar expanders at present.

SUMMARY

The technical problems to be solved: in view of the shortcomings of the related art, the present disclosure relates to a drilling fluid inhibition evaluation device and a usage method thereof which can simulate an in-situ stress condition, evaluate hydration expansion characteristics of a rock sample indoors, preferably select an inhibitor for drilling fluid, improve performances of the drilling fluid, solve the problems of vapor pressure errors and fluid state changes caused by a greater temperature difference between the fluid and an environment in conventional similar devices, and perform detailed investigation on structure changes of the sample during the expansion evaluation process.

The technical scheme provided by the present disclosure is that a drilling fluid inhibition evaluation device according to an embodiment of the present disclosure includes:

a main test member, a gas source, a circulation heating system, a central control system and a computer, the main test member connected with the gas source, a first circulation pipeline in the circulation heating system circularly extending into the main test member, the main test member electrically connected with the central control system and the computer in turn; all a temperature control pressurization system, a confining pressure pump, an ultrasonic detector and a safety valve arranged outside of the main test member, the main test member connected with the confining pressure pump; a probe of the ultrasonic detector arranged within the main test member; the temperature control pressurization system arranged between the main test member and the gas source and connected with both the main test member and the gas source, and electrically connected with the central control system; the safety valve arranged on a direct connection pipeline that is formed between the temperature control pressurization system and the main test member; the main test member including a pressure-bearing cup, a pressure-bearing bracket, a measuring rod, a rock sample cup shell and a dial indicator; the pressure-bearing cup including a main cavity at an upper part thereof, and a temperature rising cavity at a bottom part thereof, a step-shaped inner-ring bulge arranged between the main cavity and the temperature rising cavity; a rock sample cup that is formed by the rock sample cup shell and a rock sample cup cover, placed on the inner-ring bulge, and a sample block arranged on the rock sample cup cover at the bottom of the rock sample cup; the pressure-bearing bracket fixed above the pressure-bearing cup, a sealing ring arranged between the pressure-bearing cup and the pressure-bearing bracket, a supporting seat arranged at the top of the pressure-bearing bracket, a fixer arranged at a lower part of the supporting seat, and the dial indicator passing through the supporting seat to be in contact with a transmission block that is slidably connected with the inside of the fixer; and the measuring rod vertically passing through a movable sealing block that completely seals a connection portion formed between the pressure-bearing cup and the pressure-bearing bracket, and then extending into the pressure-bearing cup, a bottom of the measuring rod clamped with an expansion piston above the sample block, and a top of the measuring rod in contact with a transmission block inside the fixer.

Wherein the pressure-bearing cup includes a confining pressure head, a temperature measuring probe, an outlet valve and an inlet valve that pass through a cup wall thereof, all the confining pressure head, the temperature measuring probe and the outlet valve arranged in the main cavity at the upper part of the pressure-bearing cup, and the inlet valve arranged in the temperature rising cavity at the bottom part of the pressure-bearing cup.

Wherein a confining pressure bag lined with steel wires is sleeved on an inner wall of the rock sample cup, the confining pressure bag passing through the rock sample cup shell and detachably connected with the confining pressure head through a confining pressure bag joint, and the confining pressure head connected with the confining pressure pump.

Wherein a telescopic supporting rod is connected above the measuring rod in a damping manner, and a fastening head arranged at a connection joint between the supporting rod and the measuring rod; an ultrasonic probe coaxially arranged inside the measuring rod and passing through the expansion piston to be in contact with the sample block, and then electrically connected with the external ultrasonic detector through a fastening block being arranged on a surface of the measuring rod.

Wherein an intake valve is arranged on the pressure-bearing bracket, and passes through a gas pipeline of the pressure-bearing bracket to communicate with the inside of the rock sample cup.

Wherein a temperature raising pipeline is arranged inside the temperature raising cavity and connected with the circulation heating system, and the temperature raising pipeline detachably passing through the wall of the pressure-bearing cup.

Wherein the inner-ring bulge includes a connection hole communicated between the main cavity and the temperature rising cavity.

Wherein the temperature control pressurization system includes a gas chamber, a liquid chamber and a buffer chamber arranged therein, the gas chamber connected with the gas source and connected with the liquid chamber through a first pipeline that provides with a gas-line valve, and a barometer arranged on the first pipeline thereof; the liquid chamber connected with the buffer chamber through a second pipeline that provides with a first pressure switch thereof, and the liquid chamber communicated with the outside through a liquid valve; the buffer chamber communicated with the inlet valve of the main test member through a third pipeline that provides with a second pressure switch thereof; heating pipelines arranged inside of each of the gas chamber, the liquid chamber and the buffer chamber to communicate with a second circulation pipeline.

Wherein the temperature control pressurization system includes a temperature and pressure control member electrically connected with thermocouples arranged inside the gas chamber, the liquid chamber and the buffer chamber, respectively, and further electrically connected with the central control system.

A usage method of the above drilling fluid inhibition evaluation device includes the following steps:

step 1), screwing the rock sample cup cover to the bottom of the rock sample cup shell to form the rock sample cup, measuring a depth of the rock sample cup by using a measuring tool, preparing the rock sample according to an experimental requirement thereof, for example, the rock sample is pressed by rock powder or drilled directly from a core, placing the rock sample that has been prepared in the rock sample cup, measuring the depth of the rock sample cup that has been filled with the rock sample by using the measuring tool again, and calculating a length of the rock sample by combining the depth of the rock sample cup;

step 2), putting the rock sample cup that has been filled with the rock sample in the pressure-bearing cup and then placing on the inner-ring bulge, placing the expansion piston on the rock sample, and then passing the bottom of the measuring rod through the movable sealing block to be clamped inside the expansion piston, connecting the confining pressure pump inside the pressure-bearing cup, arranging the sealing ring on the flange of the pressure-bearing cup, and finally fixedly connecting the flange of the pressure-bearing cup with the flange of the pressure-bearing bracket;

step 3), after the movable sealing block is fixed on the base above the flange of the pressure-bearing bracket, adjusting the top of the measuring rod to be in contact with and fixed to a lower portion of the transmission block in the fixer, and meanwhile, fixing the dial indicator to the supporting seat to enable a detection rod of the dial indicator to be in contact with and fixed to an upper part of the transmission block;

step 4), sequentially connecting the gas source, the temperature control pressurization system and the safety valve with the interior of the pressure-bearing cup through pipelines, connecting the gas source with a valve pipeline of the pressure-bearing bracket, extending the heating medium circulation pipeline of the circulation heating system into the pressure-bearing cup and the temperature control pressurization system, electrically connecting the temperature control pressurization system and the pressure-bearing cup with the central control system, respectively, electrically connecting both the dial indicator and the central control system with the computer, connecting the probe of the ultrasonic detector into the measuring rod, so as to complete a structure of the whole device;

step 5), after finishing sealing inspection of the whole device, starting the gas source to inject gas into the main test member until a pressure required by the experiment is obtained, injecting liquid and gas for test into the temperature control pressurization system to ensure that the gas pressure is higher than a gas pressure that is injected into the main test member, starting the circulation heating system to heat the gas and the liquid within the main test member and the temperature control pressurization system so as to reach a testing temperature required by the experiment, and then starting the confining pressure pump to provide a confining pressure required by the experiment for a sample to be tested;

step 6), after the internal temperature and the internal pressure of the main test member and the temperature control pressurization system are stable, starting the ultrasonic detector to perform sound wave monitoring on states of the sample inside the pressure-bearing cup;

step 7), opening a liquid inlet of the main test member and a gas-liquid pipeline switch inside the temperature control pressurization system, pressing the liquid into the main test member by utilizing a gas pressure difference between the temperature control pressurization system and the main test member, and when the internal pressure of the pressure-bearing cup is increased to an experimental target pressure, closing related pipeline switches to stop liquid injection;

step 8), according to a reading change of the dial indicator and a monitoring result of the ultrasonic detector, reflecting expansion amounts of the rock sample under the experimental temperature and the pressure conditions, to the central control system and the computer in real time, calculating an expansion rate according to the length of the rock sample, and monitoring specific internal structure changes during the expansion process of the rock sample.

The present disclosure provides the advantages as below.

1. The present disclosure provides that the temperature control pressurization system is adopted to pre-pressurize the experimental fluid at the experimental temperature and then inject the fluid into the expander, so that the gas expansion effect and the saturated vapor pressure of the experimental fluid at the experimental temperature are considered, which eliminates the pressure setting difference caused by the saturated vapor pressure of the fluid at a high temperature, and avoids the influence of the internal pressure of the expander on the saturated vapor pressure of the high-temperature fluid, to enable evaluation results of samples to be more accurate.

2. The mode of the present disclosure that the fluid is pre-heated by the temperature control pressurization system and then injected into the expander, comparing with the mode that the fluid is first injected into the expander and then pre-heated, which can effectively reduce the temperature change difference caused by the normal temperature fluid contacting with the rock sample in advance.

3. By heating the fluid in advance and applying a pressure higher than the saturated vapor pressure of the fluid, phase changes of the experimental fluid during the temperature change process can be effectively inhibited, and the change of experimental conditions caused by the change of fluid concentration that the instant evaporation of the normal temperature fluid directly contacts with the wall of the high-temperature cup, can be avoided.

4. The main test member is provided with the external confining pressure pump and the ultrasonic detector, on one hand, the influence caused by confining pressures of the rock sample under an original formation pressure can be freely simulated according to real formation conditions, and an expansion state of the sample under the confining pressure state can be inspected; on the other hand, according to reflection conditions of sound waves, change characteristics of pore structures of rock samples can be monitored in real time from a process that the experimental fluid contacts with the rock sample, to a process that the fluid permeates into the rock sample, and a subsequent expansion process.

5. The present disclosure provides an O-shaped ring for sealing the device, which has high wear resistance, temperature resistance and pressure resistance and good sealing performances.

6. All data of temperatures, pressures and rock sample changes are processed and analyzed by the central control system and the computer, which has high automation and accuracy.

BRIEF DESCRIPTION OF THE DRAWINGS

In order to more clearly understand the technical solution hereinafter in embodiments of the present disclosure, a brief description to the drawings used in detailed description of embodiments hereinafter is provided thereof. Obviously, the drawings described below are some embodiments of the present disclosure, for one of ordinary skill in the related art, other drawings can be obtained according to the drawings below on the premise of no creative work.

The element labels according to the embodiment of the present disclosure shown as below:

1 main test member, 2 temperature control pressurization system, 3 gas source, 4 circulation heating system, a1 first circulation pipeline, 5 confining pressure pump, 6 central control system, 7 computer, 8 ultrasonic detector, 9 safety valve, 101 pressure-bearing cup, 102 pressure-bearing bracket, 103 supporting seat, 104 dial indicator, 105 fixer, 106 transmission block, 107 intake valve, 108 gas pipeline, 109 supporting rod, 110 measuring rod, 111 ultrasonic probe, 112 fastening head, 113 fastening block, 114 sealing block, 115 sealing ring, 116 rock sample cup shell, 117 rock sample cup cover, 118 confining pressure bag, 119 expansion piston, 120 sample block, 121 confining pressure bag joint, 122 confining pressure head, 123 temperature measuring probe, 124 outlet valve, 125 inlet valve, 126 temperature raising cavity, 127 temperature raising pipeline, 128 connection hole, 201 gas chamber, 202 liquid chamber, 203 buffer chamber, 204 temperature and pressure control member, 205 thermocouple, 206 liquid valve, 207 barometer, 208 gas-line valve, 209a first pressure switch, 210 heating pipeline, b main cavity, c inner-ring bulge, d rock sample cup, i connection port, e first pipeline, f second pipeline, 209b second pressure switch, g third pipeline, a2 second circulation pipeline, a3 direct connection pipeline.

DETAILED DESCRIPTION

Reference will now be made in detail to embodiments, examples of which are illustrated in the accompanying drawings. In the following detailed description, numerous specific details are set forth in order to provide a thorough understanding of the subject matter presented herein.

In order to make the objects, technical solutions and advantages of the embodiments of the present disclosure more apparent, the technical solutions of the embodiments of the present disclosure will be described clearly and completely with reference to the accompanying drawings of the embodiments of the present disclosure, and it is obvious that the described embodiments are a part of the embodiments, rather than all embodiments of the present disclosure. All other embodiments, which can be obtained by a person skilled in the art without creative work based on the embodiments of the present disclosure, are within the protection scope of the present disclosure. Thus, the following detailed description of the embodiments of the present disclosure that are provided in the drawings, is not intended to limit the scope of the present disclosure, as claimed, but is merely representative of selected embodiments of the present disclosure.

EMBODIMENTS

Figure 1:
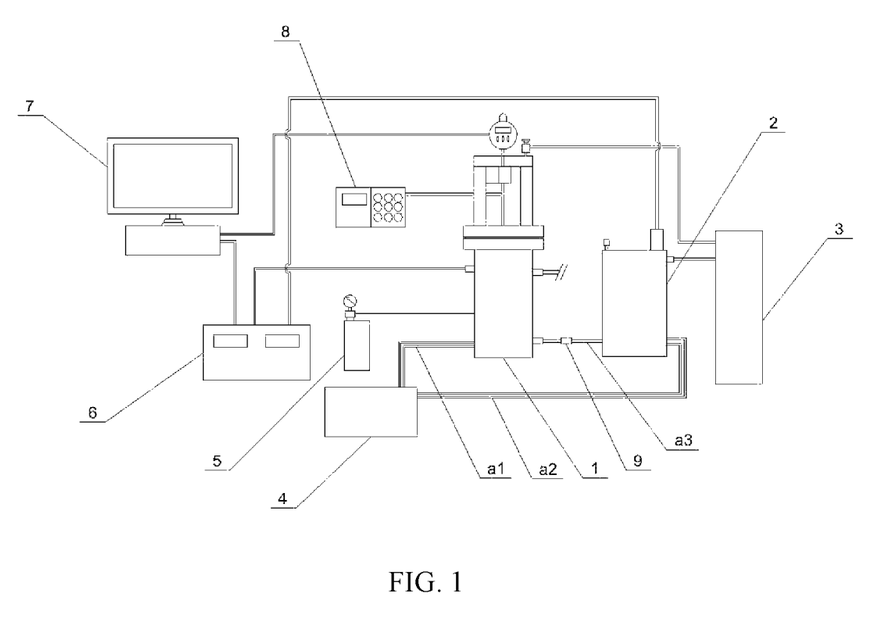
FIG. 1 is a schematic view of a drilling fluid inhibition evaluation device in accordance with an embodiment of the present disclosure.

Referring to FIGS. 1-5, a drilling fluid inhibition evaluation device includes:

a main test member 1 connected with a gas source 3 through a pipeline, a first circulation pipeline a1 in a circulation heating system 4 circularly extending into the main test member 1, the main test member 1 electrically connected with a central control system 6 and a computer 7 in turn, so that related test data in the main test member 1 can be directly transmitted back to the central control system 6 and the computer 7, and test results can be conveniently processed and analyzed. All a temperature control pressurization system 2, a confining pressure pump 5, an ultrasonic detector 8 and a safety valve 9 are arranged outside of the main test member 1, the main test member 1 connected with the confining pressure pump 5 through a pipeline, and a probe of the ultrasonic detector 8 arranged within the main test member 1. In this way, the expansion test can be performed on a rock sample by the main test member 1 under conditions of a confining pressure, a temperature and a pressure required by the experiment, and internal structure changes of the rock sample within the main test member 1 during the expansion process can be obtained through testing by the ultrasonic detector 8.

The temperature control pressurization system 2 is arranged between the main test member 1 and the gas source 3, and connected with both the temperature control pressurization system 2 and the main test member 1, and electrically connected with the central control system 6, so that internal temperatures and pressure conditions can be fed back to the central control system 6 through wires; the safety valve 9 is arranged on a direct connection pipeline a3 that is formed between the temperature control pressurization system 2 and the main test member 1, so that when high-temperature and high-pressure fluid or gas in the temperature control pressurization system 2 is transported to the main test member 1, a pressure safety range can be obtained to ensure safety of the whole device.

Figure 2:
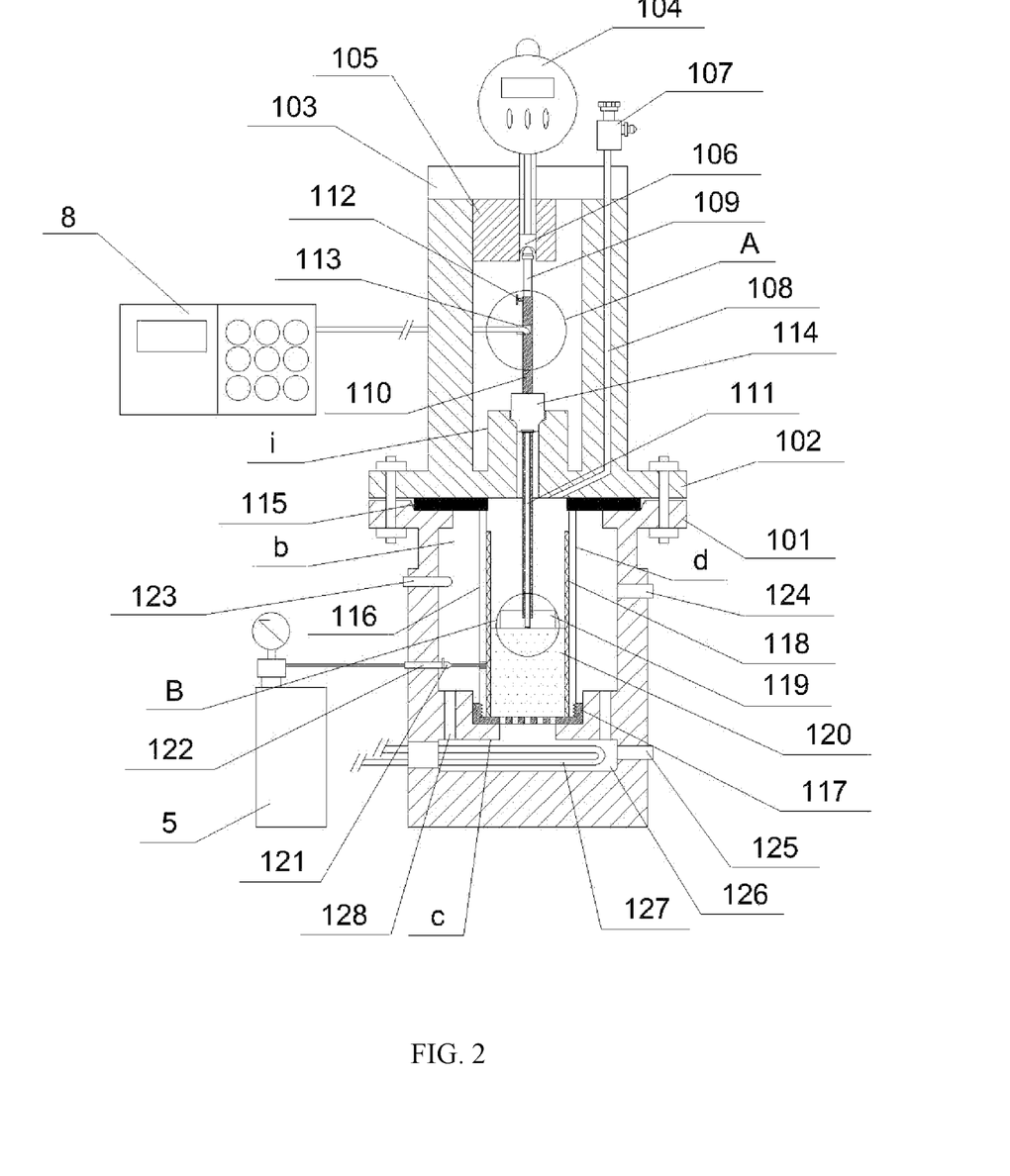
FIG. 2 is a schematic view of a main test member of the inhibition evaluation device of FIG. 1.

A stepped inner-ring bulge c is arranged between a main cavity b and a temperature rising cavity 126, to form a bracket structure for placing a rock sample cup d thereon, that is, the rock sample cup d can be stably placed on the stepped structure with edges, so that a stable test can be ensured.

The rock sample cup d that is formed by screwing threads of a rock sample cup shell 116 and a rock sample cup cover 117, is arranged on the inner-ring bulge c, filter holes distributed on the rock sample cup cover 117, a sample block 120 arranged on the rock sample cup cover 117 at the bottom of the rock sample cup d, so that the rock sample cup cover 117 is actually arranged at the bottom of the rock sample cup shell 116, to lift the sample block 120. The rock sample cup shell 116 and the rock sample cup cover 117 are screwed by the threads so as to be convenient for disassembly and cleaning the rock sample cup shell 116 and the rock sample cup cover 117 after an experiment is finished, and the filter holes on the rock sample cup cover 117 can enable the liquid within the sample block 120 to be effectively discharged, when the rock sample cup d is provided for manufacturing the sample block 120 by a pressing method.

A pressure-bearing bracket 102 is fixed above a pressure-bearing cup 101, a bottom of the pressure-bearing bracket 102 is combined with an upper part of the pressure-bearing cup 101 so as to obtain a fixed connection of the above two parts; a sealing ring 115 is arranged between the pressure-bearing bracket 102 and the pressure-bearing cup 101, the bottom of the sealing ring 115 contacts with the top of the rock sample cup d, on one hand, the sealing ring 115 plays a sealing role between the pressure-bearing bracket 102 and the pressure-bearing cup 101, on the other hand, the sealing ring 115 can also squeezedly fix with the rock sample cup d, to ensure stability of the rock sample cup d.

a supporting seat 103 is arranged at the top of the pressure-bearing bracket 102, a fixer 105 arranged at a lower part of the supporting seat 103, and a dial indicator 104 passing through the supporting seat 103 to be in contact with a transmission block 106 that is slidably connected with the inside of the fixer 105. The supporting seat 103 is configured for fixing the fixer 105 at the lower part thereof, and the dial indicator 104 at the upper part thereof, and is further configured for providing the transmission block 106 that is in contact with the measuring rod 110 for the dial indicator 104.

The measuring rod 110 vertically passes through a movable sealing block 114 that completely seals a connection portion i formed between the pressure-bearing cup 101 and the pressure-bearing bracket 102, and then extends into the pressure-bearing cup 101, the movable sealing block 114 and the pressure-bearing bracket 102 are screwed with each other, so that a subsequent experimental device of the device can be conveniently disassembled under a condition that the sealing performance is ensured, a bottom of the measuring rod 110 is clamped with an expansion piston 119 above the sample block 120, and an axial displacement of the sample block 120 can be transmitted to the measuring rod 110 through the expansion piston 119 that is stably connected with the measuring rod 110.

The top of the measuring rod 110 is in contact with the transmission block 106 inside the fixer 105, so that the axial displacement of the supporting rod 109 can be transmitted to the dial indicator 104 through the transmission block 106 and reflected by the dial indicator 104, because both the top of the supporting rod 109 and the probe of the dial indicator 104 are long strips, which are not conveniently in contact therebetween; the transmission block 106 with a large use area is to form indirect contact between the supporting rod 109 and the dial indicator 104, so that the transmission effect of the axial displacement of the supporting rod 109 to the dial indicator 104 can be improved.

The pressure-bearing cup 101 includes a confining pressure head 122, a temperature measuring probe 123, an outlet valve 124 and an inlet valve 125 that pass through a cup wall thereof, all the confining pressure head 122, the temperature measuring probe 123 and the outlet valve 124 arranged in the main cavity b at the upper part of the pressure-bearing cup 101, and the inlet valve 125 arranged in the temperature rising cavity 126 at the bottom part of the pressure-bearing cup 101, and the confining pressure head 122 is configured for connecting the external confining pressure pump 5 and the inside of the pressure-bearing cup 101. The temperature measuring probe 123 is directly and electrically connected with the central control system 6, and is configured for reflecting the temperature inside the pressure-bearing cup 101 to the central control system 6 and the computer 7 in real time; the outlet valve 124 is arranged at the upper part of the pressure-bearing cup 101 and is connected with the main cavity b, so that liquid can be discharged conveniently; the inlet valve 125 is connected to the temperature rising cavity 126 and the temperature control pressurization system 2, so that the liquid conveyed from the temperature control pressurization system 2 can directly supplement heat in the temperature rising cavity 126, thereby facilitating to maintain the temperature of the experimental fluid and avoiding errors caused by temperature changes as much as possible.

A confining pressure bag 118 lined with steel wires is sleeved on an inner wall of the rock sample cup d, the confining pressure bag 118 passing through the rock sample cup shell 116 and detachably connected with the confining pressure head 122 through a confining pressure bag joint 121, and the confining pressure head 122 connected with the confining pressure pump 5 outside of the pressure-bearing cup 101 through a pipeline. The confining pressure bag 118 is sleeved on an inner surface of the rock sample cup shell 116, so that the confining pressure bag 118 directly contacts with the sample block 120; because the confining pressure bag 118 is connected with the external confining pressure pump 5, when the external confining pressure pump 5 injects pressures into the confining pressure bag 118, a radial confining pressure surrounding the periphery of the sample block 120 is generated, so as to simulate the condition that the sample block 120 is subjected to a confining pressure under an actual underground situation; the confining pressure bag 118 is detachably connected with the confining pressure head 122, so that the confining pressure bag 118 can move along with the rock sample cup shell 116; the steel wire that is embedded in the confining pressure bag 118 can support the confining pressure bag 118, so that the confining pressure bag 118 fits well on the inner surface of the rock sample cup shell 116 by a cylindrical structure thereof. When the confined pressure is not added, the steel wire supports the confining pressure bag 118 to maintain the cylindrical structure thereof, so that the confining pressure bag 118 will not be flattened by the sample block 120, resulting in possible failure to be expanded, at the same time, it can also avoid the confining pressure bag 118 from falling off of the inner wall of the rock sample cup 116 due to lack of being supported. When the confining pressure is added inside the confining pressure bag 118, the confining pressure liquid provided by the confining pressure pump 5 will squeeze the sample block 120, and the steel wire will not affect states of the sample block 120 by the confining pressure.

The telescopic supporting rod 109 is connected above the measuring rod 110 in a damping manner, and a fastening head 112 arranged at a connection joint of the supporting rod 109 and the measuring rod 110; the supporting rod 109 is connected with the measuring rod 110 in a damping mode, so that the supporting rod 109 can be contracted into the measuring rod 110, and a telescopic length required by the supporting rod 109 within the measuring rod 110 can be determined according to a position of the transmission block 106, after the length is determined, the position of the supporting rod 109 can be fixed by rotating the fastening head 112, so that the axial displacement of the sample block 120 can be accurately transmitted to the dial indicator 104.

An ultrasonic probe 111 is coaxially arranged inside the measuring rod 110 and passes through the expansion piston 119 to be in contact with the sample block 120, and then is electrically connected with the external ultrasonic detector 8 through a fastening block 113 that is arranged on a surface of the measuring rod 110. The inside of the measuring rod 110 is hollow, the supporting rod 109 accommodated in the part of the measuring rod 110 above the fastening block 113, and the ultrasonic probe 111 accommodated in the lower part of the measuring rod 110, the fastening block 113 arranged on the surface of the measuring rod 110 and communicated with the hollow inside of the measuring rod 110 and the outside, to fix the ultrasonic probe 111, so that the ultrasonic probe 111 can be stably in contact with the surface of the sample block 120 along with the measuring rod 110, and transmit an ultrasonic detection result of the sample block 120 to the ultrasonic detector 8.

An intake valve 107 is arranged on the pressure-bearing bracket 102, and passes through a gas pipeline 108 of the pressure-bearing bracket 102 to communicate with the inside of the pressure-bearing cup 101. The intake valve 107 is connected with the gas source 3, so that gas is conveyed into a closed space formed by the pressure-bearing cup 101 and the pressure-bearing bracket 102 through the gas pipe 108, so as to provide a gas pressure required for an expansion experiment in advance.

A temperature raising pipeline 127 is arranged inside the temperature raising cavity 126 and connected with the circulation heating system 4, and the temperature raising pipeline 127 detachably passing through the wall of the pressure-bearing cup 101, so that the inside of the pressure-bearing cup 101 can be heated by the circulation heating system 4. The temperature rising pipeline 127 is fixed on the pressure-bearing cup 101 in a detachable connection mode, so that the pressure-bearing cup 101 can be freely used.

The inner-ring bulge c includes a connection hole 128 communicated between the main cavity b and the temperature rising cavity 126. When the rock sample cup d is arranged on the inner-ring bulge c, the temperature rising cavity 126 and the main cavity b are divided into two parts by the rock sample cup d and the inner-ring bulge c, and the connection hole 128 is arranged on the inner-ring bulge c, so that the liquid within the pressure-bearing cup 101 can flow freely.

Figure 3:
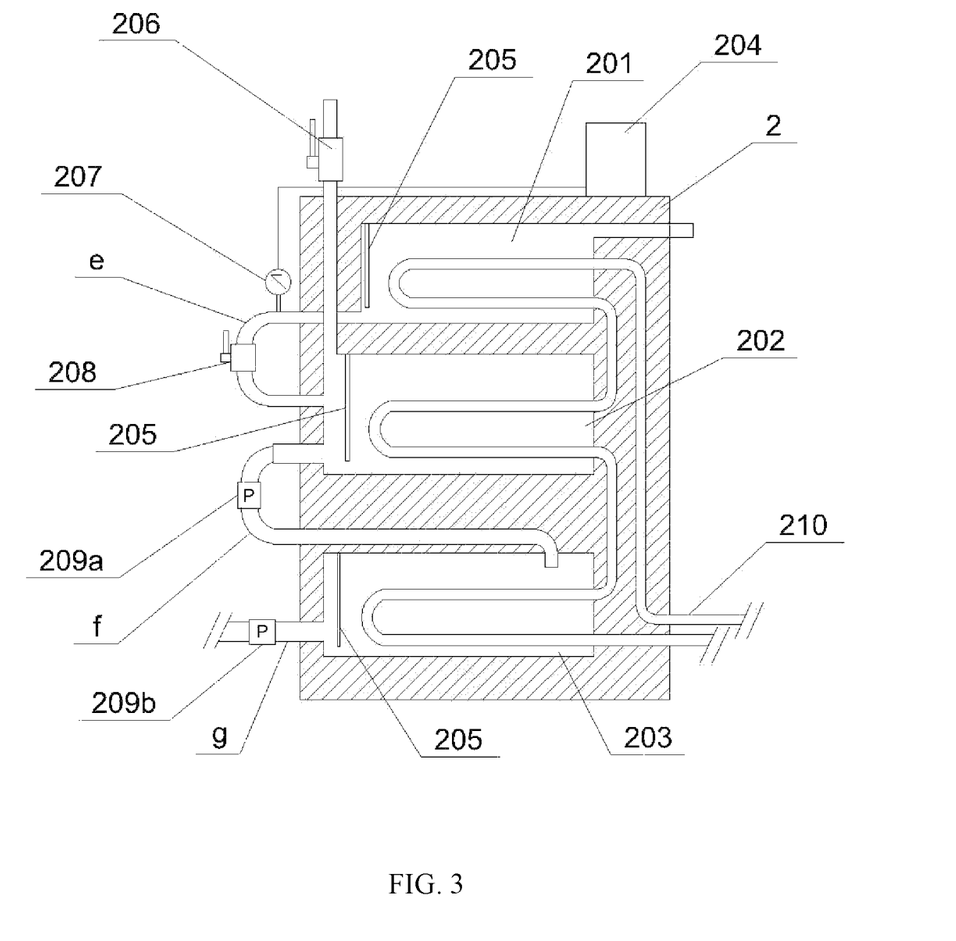
FIG. 3 is a schematic view of a temperature control pressurization system of the inhibition evaluation device of FIG. 1.
Figure 4:
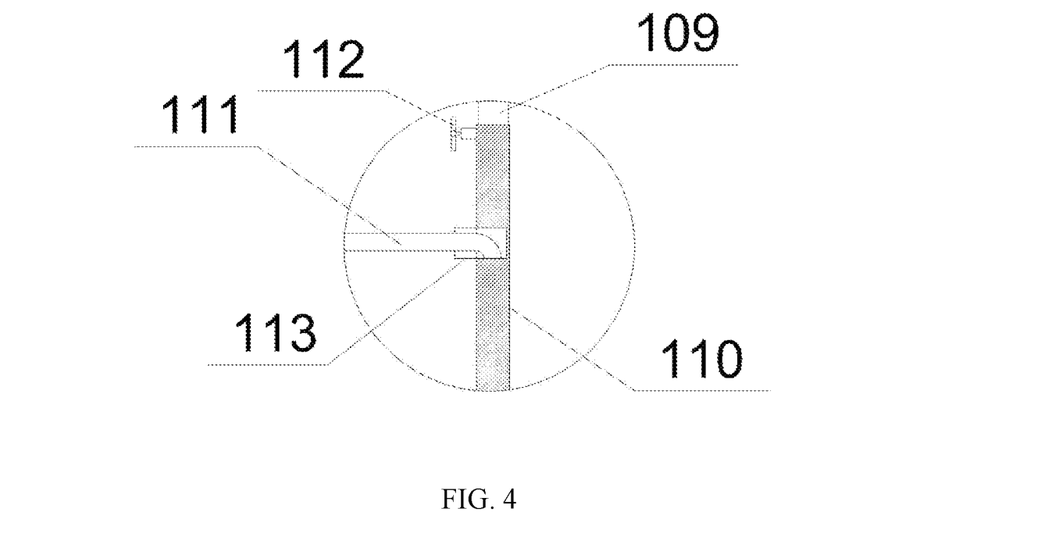
FIG. 4 is an enlarged view of circle A of FIG. 3.
Figure 5:
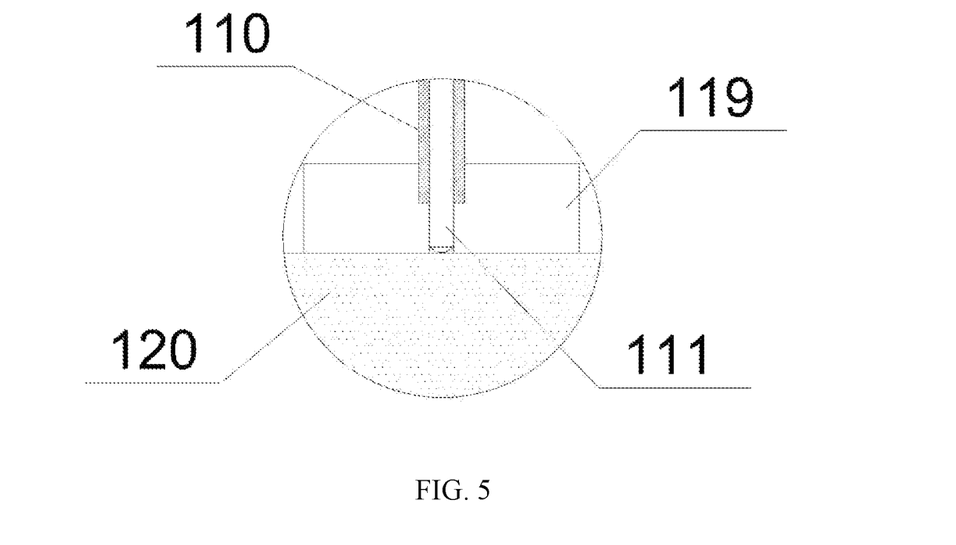
FIG. 5 is an enlarged view of circle B of FIG. 3.

The temperature control pressurization system 2 includes a gas chamber 201, a liquid chamber 202 and a buffer chamber 203 formed thereof, the gas chamber 201 connected with the gas source 3 and connected with the liquid chamber 202 through a first pipeline e that provides with a gas-line valve 208, and a barometer 207 arranged on the first pipeline e thereof; the liquid chamber 202 connected with the buffer chamber 203 through a second pipeline f that provides with a first pressure switch 209a, and the liquid chamber 202 communicated with the outside through a liquid valve 206; the buffer chamber 203 communicated with the inlet valve 125 of the main test member 1 through a third pipeline g that provides with a second pressure switch 209b; heating pipelines 210 arranged inside of each of the gas chamber 201, the liquid chamber 202 and the buffer chamber 203, to communicate with a second circulation pipeline a2. When the gas-line valve 208 is closed, the gas chamber 201 can be configured for temporarily storing gas that is introduced into the temperature control pressurization system 2 by the gas source 3, after the gas is heated to a temperature set for the experiment by the heating pipeline 210, the gas-line valve 208 can be opened to inject heating gas into the liquid chamber 202; the gas pressure is tested by the barometer 207 and then transmitted to the temperature and pressure control member 204, after the gas pressure is integrated, it is, together with other data, transmitted to the central control system 6. The liquid chamber 202 is filled with fluid for an expansion experiment through the liquid valve 206, the fluid within the liquid chamber 202 is heated to a temperature required by the experiment, the liquid valve 206 is closed before the gas-line valve 208 is opened, and then the gas-line valve 208 is opened, and the gas with the same temperature as the fluid is filled into the liquid chamber 202 through the gas chamber 201, so that the gas with a pressure higher than the saturated vapor pressure of the fluid exists above the expansion experiment fluid, so as to inhibit the change of the fluid from a liquid state to a gas state. In this way, a non-negligible influence of the saturated vapor pressure of the fluid on the pressure within a limited sealing space that is formed by the pressure-bearing cup 101 and the pressure-bearing bracket 102 is counteracted, when the fluid is directly filled into the pressure-bearing cup 101, a concentration of the fluid is kept unchanged to ensure stability of experimental conditions; the buffer chamber 203 is configured for providing a space for uniformly distributing the gas and the liquid, when the gas directly enters the liquid chamber 202 from the gas chamber 201, an interface distribution between the gas and the liquid is not uniform under an influence of gas impact, so that the pressure of the liquid surface is greatly fluctuated; after the gas and the liquid are distributed by the buffer chamber 203, a more uniform interface is formed between the gas and the liquid, so that the pressure distribution of the liquid surface is more easily controlled; in addition, the first and second pressure switches 209a, 209b are arranged on pipelines among the liquid chamber 202, the buffer chamber 203 and the pressure-bearing cup 101, so that the liquid can be sent into the pressure-bearing cup 101 only when the pressure provided by the gas for the liquid reaches the required pressure.

The temperature and pressure control member 204 is also arranged on the temperature control pressurization system 2, and electrically connected with the central control system 6 and the thermocouples 205 that are arranged in the gas chamber 201, the liquid chamber 202 and the buffer chamber 203, respectively. The thermocouples 205 are configured to automatically collect temperature change conditions in the gas chamber 201, the liquid chamber 202 and the buffer chamber 203, and then transmit the temperature change conditions to the temperature and pressure control member 204. The temperature change conditions are integrated with the pressure and other data in the temperature and pressure control member 204 and then transmitted to the central control system 6, which is convenient for the experimenters to master and adjust the operation, and effectively improves the automation and accuracy of the experiment.

In an embodiment of the present disclosure, the present disclosure provides the following steps:

step (1), screwing the rock sample cup cover 117 to the bottom of the rock sample cup shell 116 to form the rock sample cup d, and then putting the rock sample cup into a tin paper with holes, and then pasting with a filter screen.

step (2), after measuring a depth $H_0$ of the rock sample cup d by a vernier caliper, putting a sample into the rock sample cup, shaking the rock sample cup to enable an end face of the sample to be flat, and then covering a piece of tin paper with holes on a surface of the rock sample cup.

step (3), placing a film pressing rod into the rock sample cup to contact with the sample, pressing the sample with a press at 4 MPa for 5 min, taking out the film pressing rod, and measuring a depth $H_1$ of the top of the sample block 120 by the vernier caliper, to calculate a length $H_2$ of the rock sample $H_2 = H_0 - H_1$.

step (4), placing the rock sample cup d into the pressure-bearing cup 101 and on the inner-ring bulge c, the expansion piston 119 is sequentially placed above the sample block 120 in the rock sample cup d to be in contact with the tin paper with holes, passing the measuring rod 110 with the ultrasonic probe 111 through the sealing block 114 to clamp the bottom of the measuring rod in the expansion piston 119; and then, the confining pressure pump 5 is connected to the inside of the pressure-bearing cup 101, and the confining pressure bag joint 121 is buckled with the confining pressure head 122 on the wall of the pressure-bearing cup 101; then, installing the sealing ring 115 on the upper part of the pressure-bearing cup 101 so that the sealing ring 115 is in contact with the top of the rock sample cup d.

step (5), installing the pressure-bearing bracket 102 on the upper part of the pressure-bearing cup 101 to stably clamp the sealing ring 115 and connect the pressure-bearing bracket 102 with the pressure-bearing cup 101; connecting the temperature raising pipeline 127 that is configured for installing the circulation heating system 4, to the temperature raising cavity 126 at the bottom part of the pressure-bearing cup 101, and then the supporting rod 109 above the measuring rod 110 is moved to be in contact with the bottom of the transmission block 106 in the fixer 105, to ensure the supporting rod and the expansion piston 119 to be positioned on the same vertical line, and fastening the fastening head 112 to fix positions of the whole measuring rod 110 and the supporting rod 109, and meanwhile, screwing and installing the sealing block 114 on a base of the pressure-bearing bracket 102, for realizing to seal the pressure-bearing cup 101.

step (6), fixing the support seat of the dial indicator above the supporting seat 103, adjusting the probe to vertically contact with the top of the transmission block 106, and recording a reading $H_3$ of the dial indicator at the moment, that is, an initial state reading of the rock sample.

step (7), sequentially connecting the gas source 3, the temperature control pressurization system 2 and the safety valve 9 with the pressure-bearing cup 101 through pipelines, connecting the gas source 3 with a valve of the pressure-bearing bracket 102 through pipelines, extending a heating medium circulation pipeline in the circulation heating system 4 into the temperature control pressurization system 2; electrically connecting the temperature control pressurization system 2 and the pressure-bearing cup 101 with the central control system 6, respectively, and electrically connecting the dial indicator 4 and the central control system 6 with the computer 7, respectively; and stably connecting the ultrasonic meter 8 with the ultrasonic probe 111.

step (8), after completing a basic construction of the device, adding liquid with a volume of Lo into the temperature control pressurization system 2 through the liquid valve 206, wherein Lo is less than an internal volume of the liquid chamber 202 and the pressure-bearing cup 101.

step (9), closing the inlet valve 125 and the outlet valve 124 of the main test member 1 and opening the inlet valve 107 accordingly, closing the liquid valve 206 of the temperature control pressurization system 2, opening the circulation heating system 4 and monitoring a temperature of the system in real time. Through circulating heating, the temperature of the pressure-bearing cup 101 and the temperature control pressurization system 2 is synchronously increased to $T_0$, and the temperature $T_0$ is below 300° C.

step (10), using the gas source 3 to pressurize the pressure-bearing cup 101 to a pressure of $P_1$ through the intake valve 107 to make $P_1 > P_0$, so as to avoid concentration changes of the fluid caused by phase changes after the fluid enters the pressure-bearing cup 101, wherein $P_0$ is the saturated vapor pressure of the liquid in the temperature control pressurization system 2 at the temperature of $T_0$, and closing the intake valve 107; pressurizing the confining pressure bag 118 with a pressure of $P_f$ through the confining pressure pump 5, so as to apply a radial pressure $P_f$ to the sample block, and adjusting an oil pressure in real time according to changes of oil temperatures until the axial pressure is constant.

step (11), using the gas source 3 to the pressurize temperature control pressurization system 2 to a pressure of $P_2$, wherein $P_2$ satisfies: $P_2$ is under a condition of below 26 Mpa, $P_2 > P_1 > P_0$, so as to maintain stability of the phase state of the fluid in the temperature control pressurization system.

step (12), after the internal pressure and the temperature within the pressure-bearing cup 101 and the temperature control pressurization system 2 are stable, starting the ultrasonic detector 8.

step (13), opening the liquid inlet of the pressure-bearing cup 101 by using a pressure difference of $P_2 - P_1$ to press the liquid at the temperature $T_0$ into the pressure-bearing cup 101, when the pressure within the pressure-bearing cup 101 rises to a target pressure $P_3$, wherein the target pressure $P_3$ at this time satisfies: $P_2 > P_3 > P_1 > P_0$, and then closing the inlet valve 125 of the pressure-bearing cup.

step (14), according to each monitoring device, the central control system 6, the computer 7 and software, monitoring a target temperature $T_0$, the pressure $P_3$ in the device, the internal structure change of the sample block 120 during expansion and the expansion amount of the rock sample under the condition of the target pressure $P_3$ in real time.

step (15), after the experiment, recording a reading $H_4$ of the dial indicator, closing the circulation heating system 4, opening the intake valve 107, removing the additional pressure, and disassembling the device after the device is naturally cooled, wherein a final linear expansion of the rock sample is: $H_5 = H_4 - H_3$, and a final linear expansion rate of the rock sample is: $H_5/H_2$.

In the description of the present disclosure, it needs to be understood that the terms mentioned below: "upper", "below", "front", "back", "left", "right", "top", "bottom", "inner", and "outer" etc., are shown in the specification of the present disclosure. The indicated orientation or position of the terms shown in the detailed description is based on the orientation or position shown in the figures of the accompanying drawings of the present disclosure, which is only to easily simplify the description of the present disclosure, but not indicated that the devices or elements of the present disclosure should have a particular orientation or should be designed and operated in a particular orientation. So the terms illustrated in the detail description are not by way of the limitation of the present disclosure.

Although the features and elements of the present disclosure are described as embodiments in particular combinations, each feature or element can be used alone or in other various combinations within the principles of the present disclosure to the full extent indicated by the broad general meaning of the terms in which the appended claims are expressed. Any variation or replacement made by one of ordinary skill in the related art without departing from the spirit of the present disclosure shall fall within the protection scope of the present disclosure.

What is claimed is:

1. A drilling fluid inhibition evaluation device comprising a main test member, a gas source, a circulation heating system, a central control system and a computer, the main test member connected with the gas source, a first circulation pipeline in the circulation heating system circularly extending into the main test member, the main test member electrically connected with the central control system and the computer in turn; all a temperature control pressurization system, a confining pressure pump, an ultrasonic detector and a safety valve arranged outside of the main test member, the main test member connected with the confining pressure pump; a probe of the ultrasonic detector arranged within the main test member; the temperature control pressurization system arranged between the main test member and the gas source and connected with both the main test member and the gas source, and electrically connected with the central control system; the safety valve arranged on a direct connection pipeline that is formed between the temperature control pressurization system and the main test member;

the main test member comprising a pressure-bearing cup, a pressure-bearing bracket, a measuring rod, a rock sample cup shell and a dial indicator;

the pressure-bearing cup comprising a main cavity at an upper part thereof, and a temperature rising cavity at a bottom part thereof, a step-shaped inner-ring bulge arranged between the main cavity and the temperature rising cavity, a rock sample cup that is formed by the rock sample cup shell and a rock sample cup cover, placed on the inner-ring bulge, and a sample block arranged on the rock sample cup cover at the bottom of the rock sample cup;

the pressure-bearing bracket fixed above the pressure-bearing cup, a sealing ring arranged between the pressure-bearing cup and the pressure-bearing bracket, a supporting seat arranged at the top of the pressure-bearing bracket, a fixer arranged at a lower part of the supporting seat, and the dial indicator passing through the supporting seat to be in contact with a transmission block that is slidably connected with the inside of the fixer; and the measuring rod vertically passing through a movable sealing block that completely seals a connection portion formed between the pressure-bearing cup and the pressure-bearing bracket, and then extending into the pressure-bearing cup, a bottom of the measuring rod clamped with an expansion piston above the sample block, and a top of the measuring rod in contact with a transmission block inside the fixer; and wherein the pressure-bearing cup comprises a confining pressure head, a temperature measuring probe, an outlet valve and an inlet valve that pass through a cup wall thereof, all the confining pressure head, the temperature measuring probe and the outlet valve-arranged in the main cavity at the upper part of the pressure-bearing cup, and the inlet valve arranged in the temperature rising cavity at the bottom part of the pressure-bearing cup; wherein the confining pressure head is configured for connecting the external confining pressure pump and the inside of the pressure-bearing cup, the temperature measuring probe directly and electrically connected with the central control system and configured for reflecting the temperature inside the pressure-bearing cup to the central control system and the computer in real time; the liquid outlet valve arranged at the upper part of the pressure-bearing cup and connected with the main cavity and a liquid discharging external pipeline to conveniently discharge liquid; the inlet valve connected to the temperature rising cavity and the temperature control pressurization system, so that the liquid conveyed from the temperature control pressurization system is configured to directly supplement heat in the temperature rising cavity to result in facilitating to maintain the temperature of the experimental fluid and avoiding errors caused by temperature changes; and wherein a confining pressure bag lined with steel wires is sleeved on an inner wall of the rock sample cup, the confining pressure bag passing through the rock sample cup shell and detachably connected with the confining pressure head through a confining pressure bag joint, and the confining pressure head connected with the confining pressure pump; and wherein a telescopic supporting rod is connected above the measuring rod in a damping manner, and a fastening head arranged at a connection joint between the supporting rod and the measuring rod; an ultrasonic probe coaxially arranged inside the measuring rod and passing through the expansion piston to be in contact with the sample block, and then electrically connected with the external ultrasonic detector through a fastening block being arranged on a surface of the measuring rod; and wherein the ultrasonic detector is configured to monitor change characteristics of pore structures of rock samples in real time from a process that the experimental fluid contacts with the rock sample, to a process that the fluid permeates into the rock sample, and a subsequent expansion process, according to reflection conditions of sound waves.

2. The drilling fluid inhibition evaluation device as claimed in claim 1, wherein an intake valve is arranged on the pressure-bearing bracket, and passes through a gas pipeline of the pressure-bearing bracket to communicate with the inside of the rock sample cup.

3. The drilling fluid inhibition evaluation device as claimed in claim 2, wherein a temperature raising pipeline is arranged inside the temperature raising cavity and connected with the circulation heating system, and the temperature raising pipeline detachably passing through the wall of the pressure-bearing cup.

4. The drilling fluid inhibition evaluation device as claimed in claim 3, wherein the inner-ring bulge comprises a connection hole communicated between the main cavity and the temperature rising cavity.

5. The drilling fluid inhibition evaluation device as claimed in claim 4, wherein the temperature control pressurization system comprises a gas chamber, a liquid chamber and a buffer chamber arranged therein, the gas chamber connected with the gas source and connected with the liquid chamber through a first pipeline that provides with a gas-line valve, and a barometer arranged on the first pipeline thereof; the liquid chamber connected with the buffer chamber through a second pipeline that provides with a first pressure switch thereof, and the liquid chamber communicated with the outside through a liquid valve; the buffer chamber communicated with the inlet valve of the main test member through a third pipeline that provides with a second pressure switch thereof; heating pipelines arranged inside of each of the gas chamber, the liquid chamber and the buffer chamber communicated with a second circulation pipeline; and wherein when the gas-line valve is closed, the gas chamber is configured for temporarily storing gas that is introduced into the temperature control pressurization system by the gas source, after the gas is heated to a temperature set for the experiment by the heating pipeline, the gas-line valve is opened to inject heating gas into the liquid chamber; the gas pressure is tested by the barometer and transmitted to the temperature and pressure control member, and then integrated together with other data transmitted to the central control system; the liquid chamber filled with fluid for an expansion experiment through the liquid valve, when the fluid within the liquid chamber is heated to a temperature required by the experiment, the liquid valve is closed before the gas-line valve is opened, and then the gas-line valve is opened, and the gas with the same temperature as the fluid is filled into the liquid chamber through the gas chamber, so that the gas with a pressure higher than the saturated vapor pressure of the fluid exists above the expansion experiment fluid, so as to inhibit the change of the fluid from a liquid state to a gas state.

6. The drilling fluid inhibition evaluation device as claimed in claim 5, wherein the temperature control pressurization system comprises a temperature and pressure control member electrically connected with thermocouples arranged inside the gas chamber, the liquid chamber and the buffer chamber, respectively, and further electrically connected with the central control system; and wherein the thermocouples are configured to automatically collect temperature change conditions in the gas chamber, the liquid chamber and the buffer chamber, and then transmit the temperature change conditions to the temperature and pressure control member.

* * * * *